(12) United States Patent
Sun et al.

(10) Patent No.: US 12,097,039 B2
(45) Date of Patent: Sep. 24, 2024

(54) HYDRATION ASSESSMENT USING A SENSOR

(71) Applicant: VIAVI Solutions Inc., San Jose, CA (US)

(72) Inventors: Lan Sun, Santa Rosa, CA (US); Chang Meng Hsiung, Redwood City, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 116 days.

(21) Appl. No.: 16/523,167

(22) Filed: Jul. 26, 2019

(65) Prior Publication Data

US 2021/0022663 A1    Jan. 28, 2021

(51) Int. Cl.
*A61B 5/00*    (2006.01)

(52) U.S. Cl.
CPC ............ *A61B 5/443* (2013.01); *A61B 5/0002* (2013.01); *A61B 5/0075* (2013.01); *A61B 5/4519* (2013.01); *A61B 5/486* (2013.01); *A61B 5/4875* (2013.01); *A61B 5/6815* (2013.01); *A61B 5/6824* (2013.01); *A61B 5/6826* (2013.01); *A61B 5/6828* (2013.01)

(58) Field of Classification Search
CPC ..... A61B 5/486; A61B 5/0002; A61B 5/0059; A61B 5/0062; A61B 5/0071; A61B 1/00013; A61B 5/0017; A61B 5/443; A61B 5/4875; A61B 5/4519; G16H 20/60
USPC .................................................. 600/476, 306
See application file for complete search history.

(56) References Cited

U.S. PATENT DOCUMENTS

| | | | |
|---|---|---|---|
| 8,909,310 B2 * | 12/2014 | Lamego | A61B 5/02427 600/310 |
| 9,591,975 B2 * | 3/2017 | Dalvi | A61B 5/14551 |
| 2006/0058683 A1 * | 3/2006 | Chance | A61B 5/6834 600/407 |
| 2008/0221412 A1 * | 9/2008 | Baker, | A61B 5/4869 600/310 |
| 2010/0087720 A1 * | 4/2010 | Addison | A61B 5/14551 600/345 |
| 2010/0140461 A1 * | 6/2010 | Sprigle | G02B 5/201 250/226 |
| 2013/0123588 A1 | 5/2013 | Baker, Jr. | |
| 2013/0210058 A1 * | 8/2013 | White | A61B 5/443 435/29 |

(Continued)

FOREIGN PATENT DOCUMENTS

WO    WO-2013014470 A1 *    1/2013    ............ A61B 5/021

OTHER PUBLICATIONS

Woo et al., "Development of a method for the determination of human skin moisture using a portable near-infrared system", 2001, Analytical Chemistry, 73, 20, pp. 4964-4971. (Year: 2001).*

(Continued)

*Primary Examiner* — Charles A Marmor, II
*Assistant Examiner* — Raymond P Dulman
(74) *Attorney, Agent, or Firm* — Harrity & Harrity, LLP

(57) ABSTRACT

A device may obtain absorption spectra data associated with tissue of a subject. The device may determine, based on the absorption spectra data, an estimate of a water content associated with the tissue. The device may determine, based on the estimate of the water content, an estimate of a hydration level of the subject. The device may perform one or more actions based on the estimate of the hydration level of the subject.

20 Claims, 6 Drawing Sheets

(56) References Cited

U.S. PATENT DOCUMENTS

| | | | | |
|---|---|---|---|---|
| 2014/0155760 | A1* | 6/2014 | Ridder | A61B 5/1171 |
| | | | | 600/479 |
| 2014/0171759 | A1* | 6/2014 | White | A61B 5/4875 |
| | | | | 600/306 |
| 2014/0358012 | A1* | 12/2014 | Richards | H04W 4/027 |
| | | | | 600/479 |
| 2015/0088002 | A1 | 3/2015 | Podhajsky et al. | |
| 2015/0148623 | A1 | 5/2015 | Benaron | |
| 2015/0148636 | A1* | 5/2015 | Benaron | A61B 5/7207 |
| | | | | 600/328 |
| 2015/0313541 | A1 | 11/2015 | Rymut | |
| 2016/0220184 | A1* | 8/2016 | Manion | A61B 5/4266 |
| 2017/0164848 | A1* | 6/2017 | Nadeau | A61B 5/14552 |
| 2017/0319131 | A1* | 11/2017 | Xavier Da Silveira | |
| | | | | A61B 5/14546 |
| 2018/0070850 | A1* | 3/2018 | Stafford | A61B 5/0537 |
| 2019/0015023 | A1* | 1/2019 | Monfre | A61B 5/0075 |
| 2019/0021606 | A1 | 1/2019 | Martin et al. | |

OTHER PUBLICATIONS

Szakiel. "Divergences in instrumental examination results and results of sensory analysis of skin hydration after application of moisturizing cosmetic emulsions", 2016, In Wasilewski T. (Eds.), Quality of selected cosmetics and household chemistry products (pp. 11-20). Wydawnictwo Naukowe Instytutu. (Year: 2016).*

Chen et al. "Ridge penalized logistical and ordinal partial least squares regression for predicting stroke deficit from infarct topography", 2010, J. Biomedical Science and Engineering, 3, pp. 568-575 (Year: 2010).*

Lapray, P. J., Wang, X., Thomas, J. B., & Gouton, P. (2014). Multispectral filter arrays: Recent advances and practical implementation. Sensors, 14(11), 21626-21659. (Year: 2014).*

International Search Report and Written Opinion for Application No. PCT/US2020/070306, mailed on Oct. 8, 2020, 10 pages.

* cited by examiner

HYDRATION ASSESSMENT USING A SENSOR

BACKGROUND

Optical sensors are used in a variety of devices, such as image sensors, ambient light sensors, proximity sensors, hue sensors, ultraviolet (UV) sensors, and/or the like to convert optical signals into electrical signals, thereby allowing detection of optical signals or image capture. A multispectral sensor device may be utilized to capture information regarding multiple wavelengths of light. For example, the multispectral sensor device may capture information relating to a particular set of electromagnetic frequencies. The multispectral sensor device may include a set of sensor elements (e.g., optical sensors, spectral sensors, and/or image sensors) that capture the information. For example, an array of sensor elements may be utilized to capture information relating to multiple frequencies. A particular sensor element, of the sensor element array, may be associated with a filter that restricts a range of frequencies that are directed toward the particular sensor element. Such filters may be used for increasing spectral ranges as use cases require increasing ranges of spectra for sensing.

SUMMARY

According to some implementations, a device may include one or more memories and one or more processors, communicatively coupled to the one or more memories, to obtain absorption spectra data associated with tissue of a subject, wherein the absorption spectra data is obtained for a plurality of wavelength channels; determine, based on the absorption spectra data and using a tissue absorption model, an estimate of a water content associated with the tissue; determine, based on the estimate of the water content, an estimate of a hydration level of the subject; and perform one or more actions based on the estimate of the hydration level of the subject.

According to some implementations, a non-transitory computer-readable medium may store one or more instructions that, when executed by one or more processors, cause the one or more processors to obtain absorption spectra data associated with tissue of a subject; perform a fitting of the absorption spectra data to a tissue absorption model; determine, based on the fitting, an estimate of a water content associated with the tissue; determine, based on the estimate of the water content, an estimate of a hydration level of the subject; and perform one or more actions based on the estimate of the hydration level of the subject.

According to some implementations, a method may include obtaining, by a device, absorption spectra data associated with tissue of a subject; determining, by the device and based on the absorption spectra data, an estimate of a water content associated with the tissue; determining, by the device and based on the estimate of the water content, an estimate of a hydration level of the subject; and performing, by the device, one or more actions based on the estimate of the hydration level of the subject.

DETAILED DESCRIPTION

The following detailed description of example implementations refers to the accompanying drawings. The same reference numbers in different drawings may identify the same or similar elements.

The water content of a subject's tissue (e.g., skin tissue, muscle tissue, and/or the like) may provide information relating to a hydration level of the subject. For example, the water content may indicate whether the subject is dehydrated or hyperhydrated. Dehydration may decrease cognition and physical capabilities of the subject, while hyperhydration may indicate that the subject is afflicted with a disease of the heart, liver, or kidneys.

Current techniques use invasive procedures to measure tissue water content. For example, tissue water content may be measured using blood drawn from the subject. Accordingly, current techniques may cause discomfort to the subject and may need to be performed in a clinical setting. As a result, continuous monitoring of the subject's tissue water content is impractical, or impossible, according to current techniques, thereby making real-time detection of dehydrated or hyperhydrated conditions difficult.

According to some implementations described herein, a hydration assessment device may estimate tissue water content of a subject based on absorption spectra data associated with tissue of the subject. In some implementations, the hydration assessment device may obtain the absorption spectra data from a multispectral sensor device (e.g., a binary multispectral sensor (BMS) device) in contact with a skin surface of the subject. The hydration assessment device may use the absorption spectra data to estimate a water content of the subject's tissue, and may use the estimate of the water content to determine an estimate of a hydration level for the subject.

In this way, the hydration assessment device facilitates efficient and accurate estimation of the subject's hydration level in a non-invasive manner. As such, the hydration assessment device improves subject compliance and conserves resources (e.g., medical device resources used to draw blood, medical equipment and processing resources used to analyze drawn blood, care provider resources, and/or the like) associated with invasive procedures. Moreover, the multispectral sensor device may be worn by the subject (e.g., on a wrist of the subject) to permit continuous monitoring of the subject's hydration level, thereby improving detection of dehydrated and hyperhydrated conditions.

Figure 1:
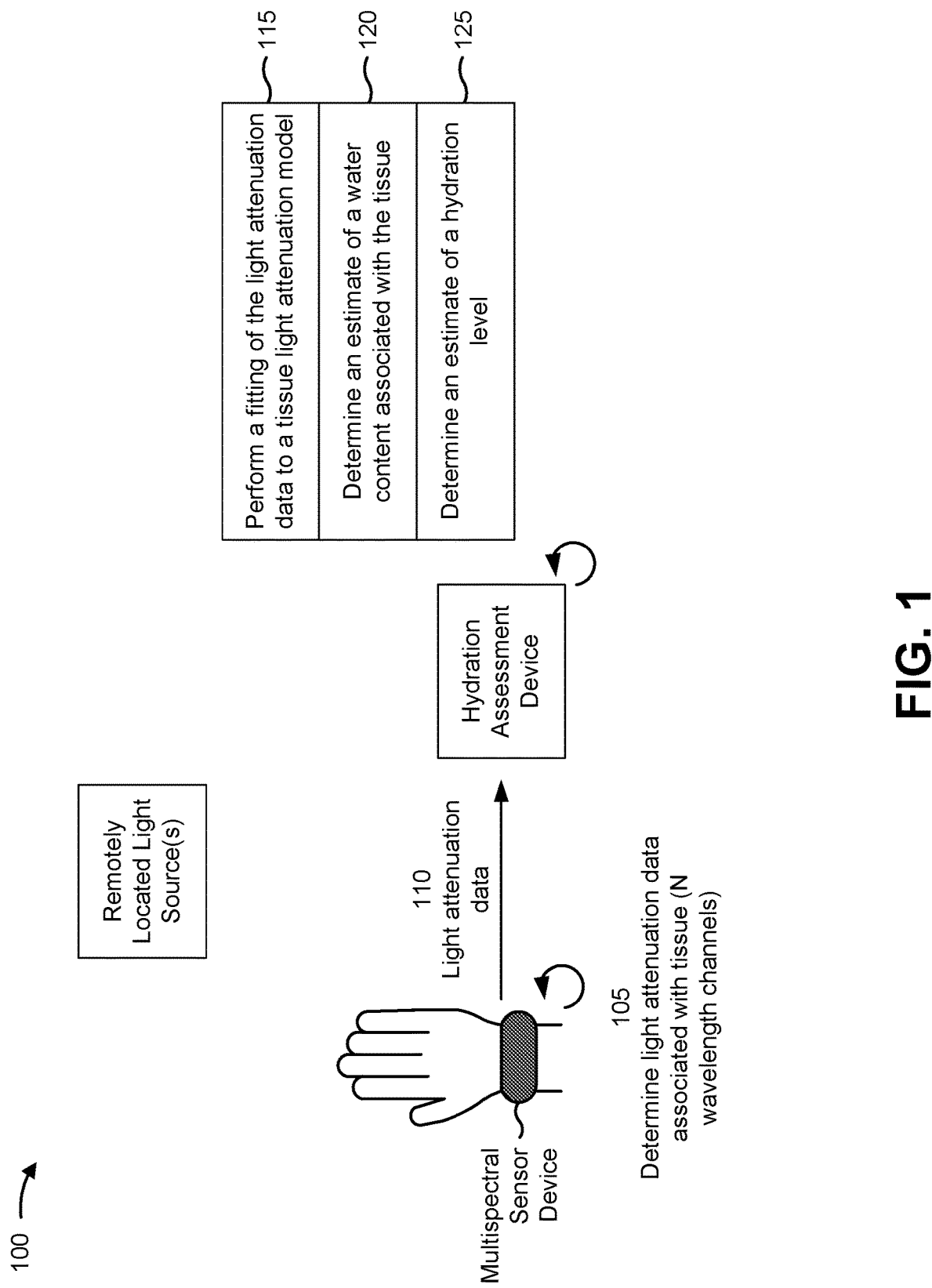
FIG. 1 is a diagram of an example implementation described herein.

FIG. 1 is a diagram of an example implementation 100 described herein. As shown in FIG. 1, a multispectral sensor device may be positioned relative to a skin surface of a subject (e.g., in contact with the skin surface of the subject). For example, as shown in FIG. 1, the multispectral sensor device may be worn on a wrist of the subject. Additionally, or alternatively, the multispectral sensor device may be positioned relative to the skin surface at another location of the subject's body, such as on a finger, an arm, a leg, an ear lobe, and/or the like. In some implementations, the multispectral sensor device includes a BMS device that operates in, for example, the visible (VIS) spectrum, the near-infrared (NIR) spectrum (e.g., 750 nanometers to 1400 nanometers), and/or the like.

As shown by reference number 105, the multispectral sensor device may determine (e.g., measure, gather, collect, and/or the like) absorption spectra data associated with N (N>1) wavelength channels (e.g., 16 wavelength channels, 36 wavelength channels, 64 wavelength channels, and/or the like). The absorption spectra data identifies, for each of the N wavelength channels, a degree of light absorption (e.g., light attenuation) by the tissue of the subject. Accordingly, the multispectral sensor device may include a light source configured to transmit light (e.g., light in the NIR spectrum) through the tissue of the subject, a light detector that includes a plurality of light sensor elements configured to capture information relating to the light transmitted by the light source, and a multispectral filter that includes a plurality of filters (e.g., 16 filters, 36 filters, 64 filters, and/or the like), each configured to restrict a range of wavelengths that are directed toward respective light sensor elements. In some implementations, the light source may be remotely located from the multispectral sensor device. Moreover, the light source may include a plurality of light sources. For example, the light source may include one or more first light sources that are included in the multispectral sensor device and one or more second light sources that are remotely located from the multispectral sensor device.

In some implementations, the light source may be directed to a particular type of tissue of the subject. For example, the light source may be directed to a skin layer of the subject or a muscle layer of the subject based on a distance between the light source and the light detector, based on an intensity of light directed at the skin surface of the subject, and/or the like. For example, if the light detector is positioned at the skin surface of the subject, the light source may be located a first distance from the light detector (e.g., a first distance from the skin surface of the subject) in order to reach the skin layer of the subject, or a second distance from the light detector (e.g., a second distance from the skin surface of the subject) in order to reach the muscle layer of the subject. In such a case, the first distance may be shorter than the second distance. Additionally, or alternatively, multiple light sources may be selectively activated in order to produce a particular light intensity needed to reach the skin layer of the subject or the muscle layer of the subject. The distance between the light source and the light detector and/or the quantity of light sources activated may be selected by the subject and/or a care provider for the subject according to whether skin hydration assessment or muscle hydration assessment is desired, according to a muscle content and/or a fat content of the subject's tissue, and/or the like.

As shown by reference number 110, a hydration assessment device may obtain the absorption spectra data from the multispectral sensor device. The hydration assessment device is a device capable of determining a hydration level of the subject based on the absorption spectra data associated with multiple wavelength channels, as described herein. In some implementations, the hydration assessment device may be integrated with the multispectral sensor device (e.g., in a same package, in a same housing, on a same chip, and/or the like). Alternatively, the hydration assessment device may be separate (e.g., remotely located) from the multispectral sensor device.

In some implementations, the hydration assessment device may obtain the absorption spectra data in real-time or near real-time (e.g., when the multispectral sensor device is configured to provide the absorption spectra data as the multispectral sensor device obtains the absorption spectra data). Additionally, or alternatively, the hydration assessment device may obtain the absorption spectra data based on the multispectral sensor device (e.g., automatically) providing the absorption spectra data on a periodic basis (e.g., every one second, every five seconds, and/or the like). Additionally, or alternatively, the hydration assessment device may obtain the absorption spectra data from the multispectral sensor device based on requesting the absorption spectra data from the multispectral sensor device.

As shown by reference number 115, the hydration assessment device may perform a fitting of the absorption spectra data to a tissue absorption model. The tissue absorption model may provide an approximation of light attenuation in tissue by modeling light scattering and light absorption in tissue. The tissue absorption model may be a Taylor expansion attenuation model represented by Equation 1:

$$A_{model}(\lambda) = c_0 + c_1\lambda + \langle L \rangle [c_{H_2O}\varepsilon_{H_2O}(\lambda) + c_{Hb}\varepsilon_{Hb}(\lambda) + c_{HbO_2}\varepsilon_{HbO_2}(\lambda)] \quad \text{Equation 1}$$

where $c_0$ and $c_1$ are constants, $\langle L \rangle$ is the mean pathlength of the reflected light through the tissue, $\varepsilon_{H_2O}(\lambda)$, $\varepsilon_{Hb}(\lambda)$ and $\varepsilon_{HbO_2}(\lambda)$ are wavelength-dependent extinction coefficients for water, deoxygenated hemoglobin, and oxygenated hemoglobin, respectively, and $c_{H_2O}$, $c_{Hb}$, and $c_{HbO_2}$ are concentrations of water, deoxygenated hemoglobin, and oxygenated hemoglobin, respectively. The term $\langle L \rangle [c_{H_2O}\varepsilon_{H_2O}(\lambda) + c_{Hb}\varepsilon_{Hb}(\lambda) + c_{HbO_2}\varepsilon_{HbO_2}(\lambda)]$ describes light absorption by water and hemoglobin, and the term of $C_1\lambda$ describes scattering from the tissue.

The hydration assessment device may determine the values of $c_0$, $c_1$, $\langle L \rangle$, $c_{H_2O}$, $c_{Hb}$, $c_{HbO_2}$ by minimizing the sum of squared differences between modeled absorption spectra and measured absorption spectra (e.g., the absorption spectra data) with a nonlinear least squares procedure. In some implementations, the hydration assessment device may determine initial values for the tissue absorption model in order to provide a starting point for the fitting procedure. For example, the hydration assessment device may determine the initial values using a simulated annealing procedure, or another procedure for determining initial values. In some implementations, the hydration assessment device may perform the fitting procedure constrained by a logistic function that provides an upper boundary and/or a lower boundary for the values of one or more of $c_0$, $c_1$, $\langle L \rangle$, $c_{H_2O}$, $c_{Hb}$, or $c_{HbO_2}$. In some implementations, the hydration assessment device may use another model describing light absorption by tissue in a manner similar to that described above.

As shown by reference number 120, the hydration assessment device may determine an estimate of a water content of the subject's tissue. For example, the hydration assessment device may determine the estimate of the water content based on a value for the concentration of water ($c_{H_2O}$) determined from the fitting procedure. The estimate of the water content may relate to the subject's skin layer and/or muscle layer according to a distance between the light source and the light detector, as described above. In this way, the hydration assessment device facilitates efficient and non-invasive estimation of the water content of the subject's tissue.

As shown by reference number 125, the hydration assessment device may determine an estimate of a hydration level for the subject. For example, the hydration assessment device may determine the estimate of the hydration level based on the estimate of the water content. As an example, the hydration assessment device may refer to a mapping of water content and hydration levels in order to determine the estimate of the hydration level based on the estimate of the water content. As another example, the hydration assessment device may determine the estimate of the hydration level based on a model that describes a relationship between water content and hydration level. The estimate of the hydration level may relate to the subject's skin layer or muscle layer according to whether the estimate of the water content relates to the subject's skin layer or muscle layer, as described above. In some implementations, the estimate of the hydration level may estimate an overall hydration level for the subject based on a combination of an estimate of a hydration level for the subject's skin layer and an estimate of a hydration level for the subject's muscle layer. The estimate of the hydration level may be quantitative (e.g., a percentage) or qualitative (e.g., dehydrated, hydrated, hyperhydrated, and/or the like).

The hydration assessment device may perform one or more actions based on the estimate of the hydration level. In some implementations, the hydration assessment device may provide the estimate of the hydration level to permit the subject and/or a care provider for the subject to analyze the estimate of the hydration level. Additionally, or alternatively, the hydration assessment device may analyze the estimate of the hydration level, and provide a notification indicating that the subject is to consume more water, consume less water, seek medical treatment, and/or the like, if the estimate of the hydration level satisfies a particular threshold value. The hydration assessment device may provide the estimate of the hydration level and/or the notification to a display associated with the multispectral sensor device and/or the hydration assessment device, to a user device associated with the subject, to a user device associated with a care provider for the subject, and/or the like.

In some implementations, the hydration assessment device may transmit a notification to the user device associated with the subject and/or the user device associated with the care provider for the subject if the estimate of the hydration level satisfies a particular threshold value. For example, the hydration assessment device may transmit the notification when the estimate for the hydration level satisfies a threshold value associated with severe dehydration, severe hyperhydration, and/or the like. In some implementations, the hydration assessment device may cause a wearable device (e.g., a wearable device that includes the multispectral sensor device and/or the hydration assessment device) to provide a notification (e.g., an audible, haptic, and/or visual alert) if the estimate of the hydration level satisfies a particular threshold value.

In some implementations, the hydration assessment device may cause another device to regulate fluids provided to the subject if the estimate of the hydration level satisfies a particular threshold value. For example, the hydration assessment device may cause another device to provide, or cease providing, fluids to the subject based on whether the estimate of the hydration level satisfies the particular threshold value. As an example, the other device may be a device that controls intravenous therapy for the subject.

In this way, the hydration assessment device facilitates efficient and accurate assessment of the subject's hydration level. Moreover, the hydration assessment device, in connection with the multispectral sensor device, permits noninvasive assessment of the subject's hydration level, such that continuous or frequent assessment will be tolerated by the subject. Accordingly, the hydration assessment device improves detection of dehydrated or hyperhydrated conditions of the subject.

As indicated above, FIG. 1 is provided merely as an example. Other examples may differ from what is described with regard to FIG. 1.

Figure 2:
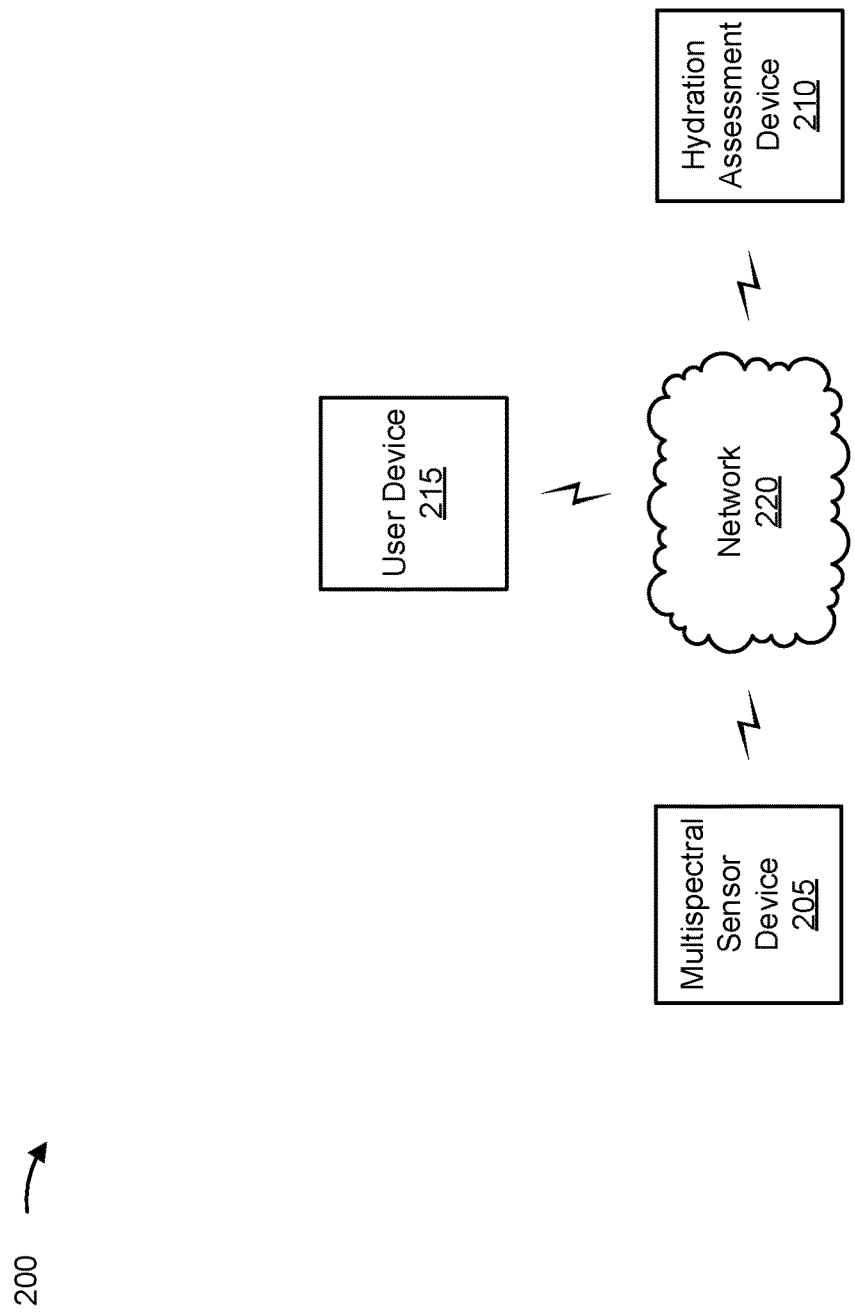
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a multispectral sensor device 205, a hydration assessment device 210, a user device 215, and a network 220. Devices of environment 200 may interconnect via wired connections, wireless connections, or a combination of wired and wireless connections.

Multispectral sensor device 205 includes a device capable of measuring, gathering, collecting, or otherwise determining absorption spectra data associated with a plurality of wavelength channels, as described herein. For example, multispectral sensor device 205 may include a multispectral sensing device capable of determining absorption data on each of 64 wavelength channels. In some implementations, multispectral sensor device 205 may operate in the visible spectrum, the near infrared spectrum, the infrared spectrum, and/or the like. In some implementations, multispectral sensor device 205 may be a wearable device (e.g., a device that can be worn on a wrist, a finger, an arm, a leg, a head, an ear, and/or the like). In some implementations, multispectral sensor device 205 may receive information from and/or transmit information to another device in environment 200, such as hydration assessment device 210.

Hydration assessment device 210 includes a device capable of determining an estimate of water content and/or an estimate of hydration level based on absorption spectra data associated with a plurality of wavelength channels, as described herein. For example, hydration assessment device 210 may include an application specific integrated circuit (ASIC), an integrated circuit, a server, a group of servers, and/or the like, and/or another type of communication and/or computing device. In some implementations, hydration assessment device 210 may be integrated with multispectral sensor device 205 (e.g., such that multispectral sensor device 205 and hydration assessment device 210 are on the same chip, in the same package, in the same housing, in the same wearable device, and/or the like). Alternatively, in some implementations, hydration assessment device 210 may be separate from multispectral sensor device 205. In some implementations, hydration assessment device 210 may receive information from and/or transmit information to another device in environment 200, such as multispectral sensor device 205.

User device 215 includes one or more devices capable of receiving, generating, storing, processing, and/or providing information associated with absorption spectra data, water content, and/or hydration level. For example, user device 215 may include a communication and/or computing device, such as a mobile phone (e.g., a smart phone, a radiotelephone, and/or the like), a laptop computer, a tablet computer, a handheld computer, a desktop computer, a gaming device, a wearable communication device (e.g., a smart wristwatch, a pair of smart eyeglasses, and/or the like), or a similar type of device. In some implementations, multispectral sensor device 205 and/or hydration assessment device 210 may be integrated with user device 215 (e.g., such that multispectral sensor device 205 and/or hydration assessment device 210 are included in a housing of user device 215).

Network 220 includes one or more wired and/or wireless networks. For example, network 220 may include a wired network (e.g., when multispectral sensor device 205 and hydration assessment device 210 are included in the same package and/or the same chip). As another example, network 220 may include a cellular network (e.g., a long-term evolution (LTE) network, a code division multiple access (CDMA) network, a 3G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The quantity and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
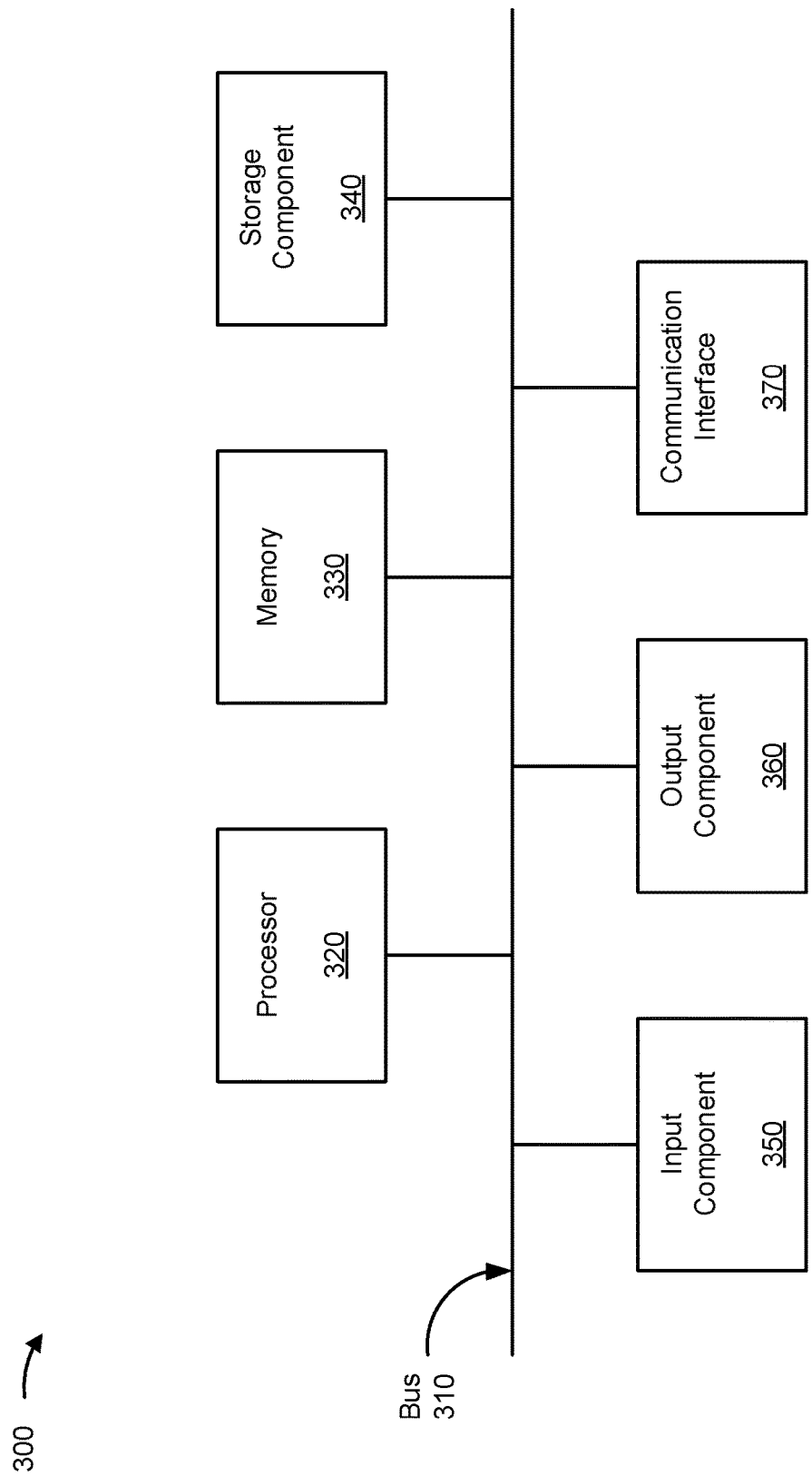
FIG. 3 is a diagram of example components of one or more devices of FIG. 2.

FIG. 3 is a diagram of example components of a device 300. Device 300 may correspond to multispectral sensor device 205, hydration assessment device 210, and/or user device 215. In some implementations, multispectral sensor device 205, hydration assessment device 210, and/or user device 215 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The quantity and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Some implementations described herein allow hydration assessment device 210 to determine, based on absorption spectra data collected by multispectral sensor device 205, an estimate of water content in tissue, which may be used by hydration assessment device 210 to generate biometric data and/or perform a biometric monitoring action. More specifically, some implementations described herein allow hydration assessment device 210 to process absorption spectra data relating to tissue of a subject in order to determine an estimate of a water content in the tissue and/or an estimate of a hydration level of the subject, thereby facilitating accurate and non-invasive biometric monitoring of the subject's hydration.

Figure 4:
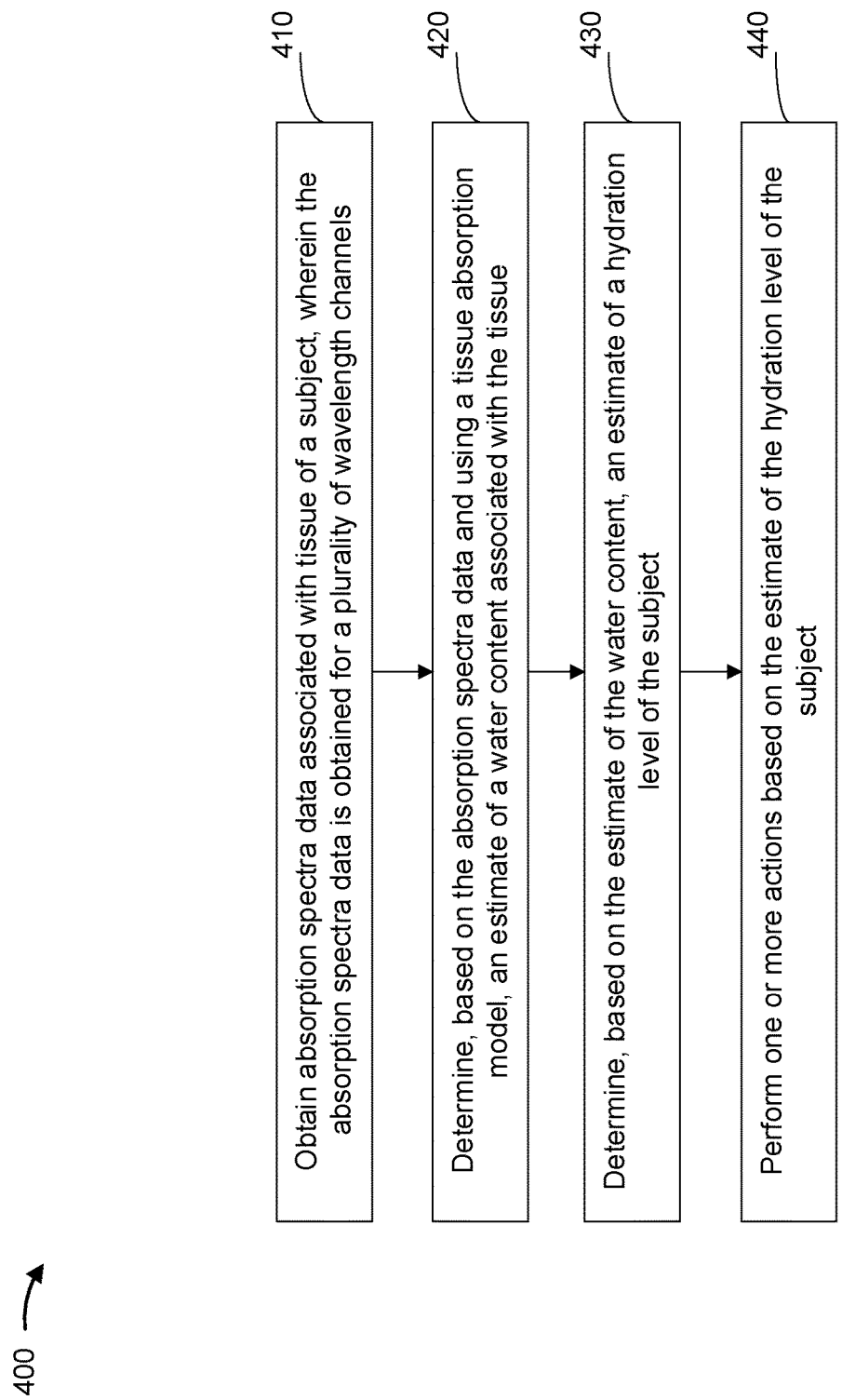
FIGS. 4-6 are flowcharts of example processes for hydration assessment.

FIG. 4 is a flow chart of an example process 400 for hydration assessment. In some implementations, one or more process blocks of FIG. 4 may be performed by a hydration assessment device (e.g., hydration assessment device 210). In some implementations, one or more process blocks of FIG. 4 may be performed by another device or a group of devices separate from or including the hydration assessment device, such as a multispectral sensor device (e.g., multispectral sensor device 205), a user device (e.g., user device 215), and/or the like.

As shown in FIG. 4, process 400 may include obtaining absorption spectra data associated with tissue of a subject, wherein the absorption spectra data is obtained for a plurality of wavelength channels (block 410). For example, the hydration assessment device (e.g., using processor 320, memory 330, storage component 340, input component 350, communication interface 370, and/or the like) may obtain absorption spectra data associated with tissue of a subject, as described above. In some implementations, the absorption spectra data is obtained for a plurality of wavelength channels.

As further shown in FIG. 4, process 400 may include determining, based on the absorption spectra data and using a tissue absorption model, an estimate of a water content associated with the tissue (block 420). For example, the hydration assessment device (e.g., using processor 320, memory 330, storage component 340, and/or the like) may determine, based on the absorption spectra data and using a tissue absorption model, an estimate of a water content associated with the tissue, as described above.

As further shown in FIG. 4, process 400 may include determining, based on the estimate of the water content, an estimate of a hydration level of the subject (block 430). For example, the hydration assessment device (e.g., using processor 320, memory 330, storage component 340, and/or the like) may determine, based on the estimate of the water content, an estimate of a hydration level of the subject, as described above.

As further shown in FIG. 4, process 400 may include performing one or more actions based on the estimate of the hydration level of the subject (block 440). For example, the hydration assessment device (e.g., using processor 320, memory 330, storage component 340, input component 350, output component 360, communication interface 370, and/or the like) may perform one or more actions based on the estimate of the hydration level of the subject, as described above.

Process 400 may include additional implementations, such as any single implementation or any combination of implementations described below and/or in connection with one or more other processes described elsewhere herein.

In a first implementation, performing the one or more actions comprises at least one of providing the estimate of the hydration level, providing a notification indicating that the subject is to consume water when the estimate of the hydration level satisfies a threshold value, transmitting a notification to a user device of the subject when the estimate of the hydration level satisfies a threshold value, or transmitting a notification to a user device of a care provider for the subject when the estimate of the hydration level satisfies a threshold value.

In a second implementation, alone or in combination with the first implementation, the device includes a multispectral sensor device. In a third implementation, alone or in combination with one or more of the first and second implementations, the tissue is a skin layer based on a first distance between a light source of the multispectral sensor device and a light detector of the multispectral sensor device, or the tissue is a muscle layer based on a second distance between the light source and the light detector.

In a fourth implementation, alone or in combination with one or more of the first through third implementations, the plurality of wavelength channels are associated with near-infrared light or visible light. In a fifth implementation, alone or in combination with one or more of the first through fourth implementations, the device is configured to contact a skin surface of the subject. In a sixth implementation, alone or in combination with one or more of the first through fifth implementations, the tissue of the subject is associated with at least one of a wrist, a finger, an arm, a leg, a head, or an ear.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
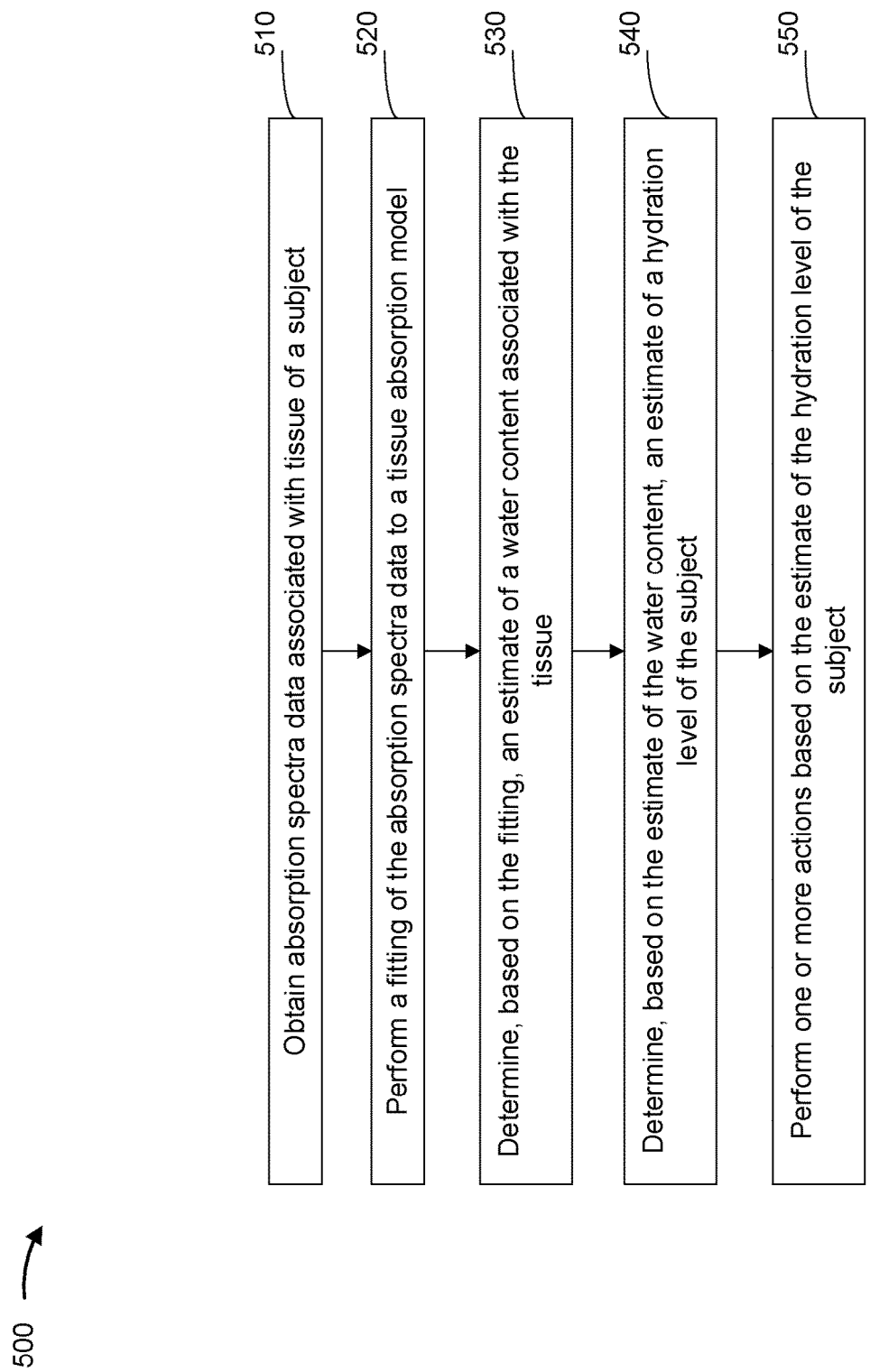

FIG. 5 is a flow chart of an example process 500 for hydration assessment. In some implementations, one or more process blocks of FIG. 5 may be performed by a hydration assessment device (e.g., hydration assessment device 210). In some implementations, one or more process blocks of FIG. 5 may be performed by another device or a group of devices separate from or including the hydration assessment device, such as a multispectral sensor device (e.g., multispectral sensor device 205), a user device (e.g., user device 215), and/or the like.

As shown in FIG. 5, process 500 may include obtaining absorption spectra data associated with tissue of a subject (block 510). For example, the hydration assessment device (e.g., using processor 320, memory 330, storage component 340, input component 350, communication interface 370, and/or the like) may obtain absorption spectra data associated with tissue of a subject, as described above.

As further shown in FIG. 5, process 500 may include performing a fitting of the absorption spectra data to a tissue absorption model (block 520). For example, the hydration assessment device (e.g., using processor 320, memory 330, storage component 340, and/or the like) may perform a fitting of the absorption spectra data to a tissue absorption model, as described above.

As further shown in FIG. 5, process 500 may include determining, based on the fitting, an estimate of a water content associated with the tissue (block 530). For example, the hydration assessment device (e.g., using processor 320, memory 330, storage component 340, and/or the like) may determine, based on the fitting, an estimate of a water content associated with the tissue, as described above.

As further shown in FIG. 5, process 500 may include determining, based on the estimate of the water content, an estimate of a hydration level of the subject (block 540). For example, the hydration assessment device (e.g., using processor 320, memory 330, storage component 340, and/or the like) may determine, based on the estimate of the water content, an estimate of a hydration level of the subject, as described above.

As further shown in FIG. 5, process 500 may include performing one or more actions based on the estimate of the hydration level of the subject (block 550). For example, the hydration assessment device (e.g., using processor 320, memory 330, storage component 340, input component 350, output component 360, communication interface 370, and/or the like) may perform one or more actions based on the estimate of the hydration level of the subject, as described above.

Process 500 may include additional implementations, such as any single implementation or any combination of implementations described below and/or in connection with one or more other processes described elsewhere herein.

In a first implementation, performing the one or more actions comprises at least one of providing the estimate of the hydration level, providing a notification indicating that the subject is not to consume water when the estimate of the hydration level satisfies a threshold value, transmitting a notification to a user device of the subject when the estimate of the hydration level satisfies a threshold value, or transmitting a notification to a user device of a care provider for the subject when the estimate of the hydration level satisfies a threshold value.

In a second implementation, alone or in combination with the first implementation, the absorption spectra data is obtained for a plurality of wavelength channels. In a third implementation, alone or in combination with one or more of the first and second implementations, the tissue absorption model models light scattering and light absorption in tissue.

In a fourth implementation, alone or in combination with one or more of the first through third implementations, the fitting of the absorption spectra data to the tissue absorption model is performed using a nonlinear least squares procedure. In a fifth implementation, alone or in combination with one or more of the first through fourth implementations, the fitting of the absorption spectra data to the tissue absorption model is constrained by a logistic function that provides a boundary for a value of the water content. In a sixth implementation, alone or in combination with one or more of the first through fifth implementations, process 500 further comprises determining, prior to performing the fitting, initial values for the tissue absorption model.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
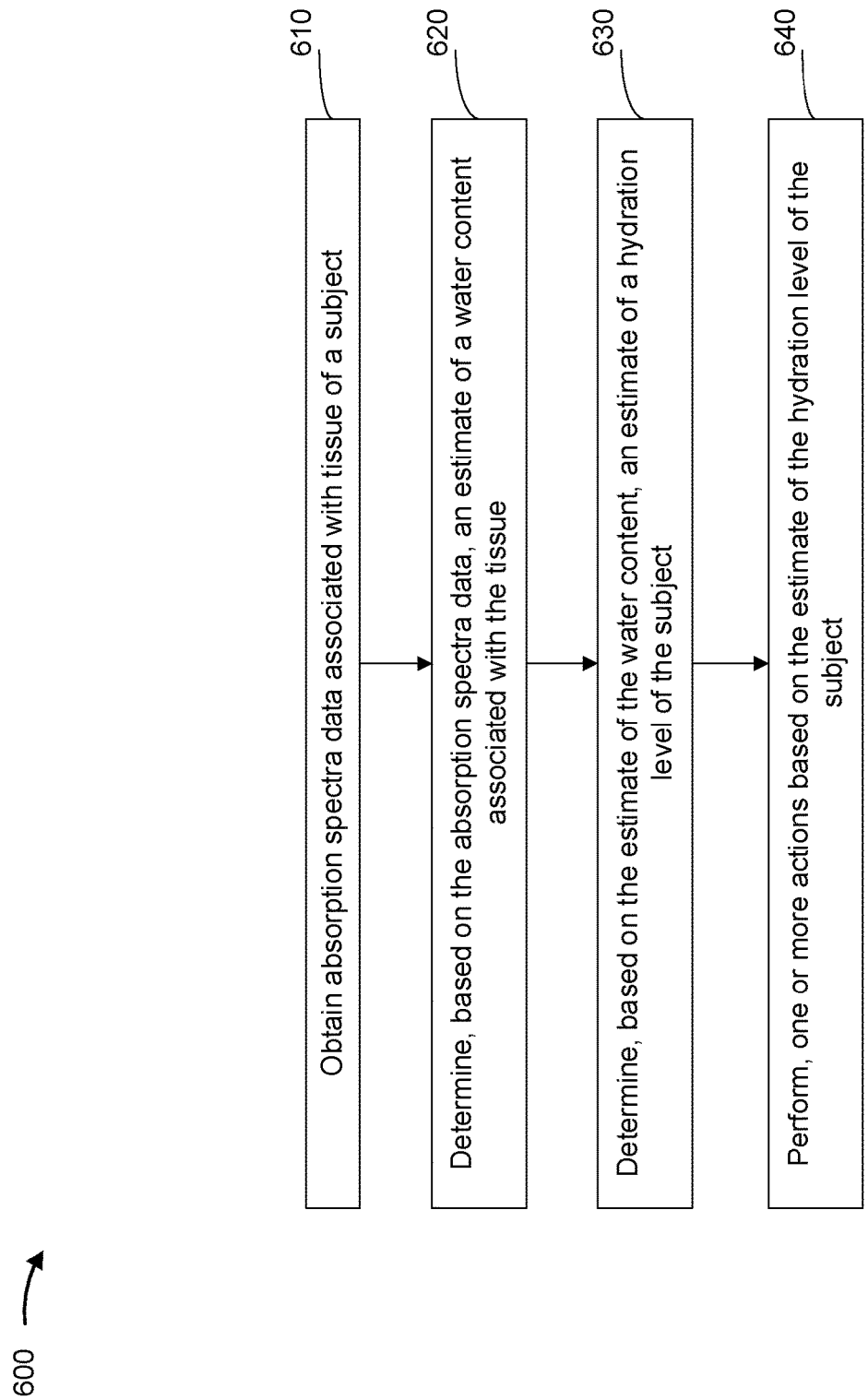

FIG. 6 is a flow chart of an example process 600 for hydration assessment. In some implementations, one or more process blocks of FIG. 6 may be performed by a hydration assessment device (e.g., hydration assessment device 210). In some implementations, one or more process blocks of FIG. 6 may be performed by another device or a group of devices separate from or including the hydration assessment device, such as a multispectral sensor device (e.g., multispectral sensor device 205), a user device (e.g., user device 215), and/or the like.

As shown in FIG. 6, process 600 may include obtaining absorption spectra data associated with tissue of a subject (block 610). For example, the hydration assessment device (e.g., using processor 320, memory 330, storage component 340, input component 350, communication interface 370, and/or the like) may obtain absorption spectra data associated with tissue of a subject, as described above.

As further shown in FIG. 6, process 600 may include determining, based on the absorption spectra data, an estimate of a water content associated with the tissue (block 620). For example, the hydration assessment device (e.g., using processor 320, memory 330, storage component 340, and/or the like) may determine, based on the absorption spectra data, an estimate of a water content associated with the tissue, as described above.

As further shown in FIG. 6, process 600 may include determining, based on the estimate of the water content, an estimate of a hydration level of the subject (block 630). For example, the hydration assessment device (e.g., using processor 320, memory 330, storage component 340, and/or the like) may determine, based on the estimate of the water content, an estimate of a hydration level of the subject, as described above.

As further shown in FIG. 6, process 600 may include performing one or more actions based on the estimate of the hydration level of the subject (block 640). For example, the hydration assessment device (e.g., using processor 320, memory 330, storage component 340, input component 350, output component 360, communication interface 370, and/or the like) may perform one or more actions based on the estimate of the hydration level of the subject, as described above.

Process 600 may include additional implementations, such as any single implementation or any combination of implementations described below and/or in connection with one or more other processes described elsewhere herein.

In a first implementation, the one or more actions comprise at least one of providing the estimate of the hydration level, providing a notification indicating that the subject is to consume water when the estimate of the hydration level satisfies a threshold value, transmitting a notification to a user device of the subject when the estimate of the hydration level satisfies a threshold value, or transmitting a notification to a user device of a care provider for the subject when the estimate of the hydration level satisfies a threshold value.

In a second implementation, alone or in combination with the first implementation, the tissue of the subject is at least one of a skin layer or a muscle layer. In a third implementation, alone or in combination with one or more of the first and second implementations, the estimate of the hydration level of the subject relates to at least one of a hydration level in a skin layer of the subject or a hydration level in a muscle layer of the subject. In a fourth implementation, alone or in combination with one or more of the first through third implementations, the absorption spectra data is obtained for a plurality of wavelength channels. In a fifth implementation, alone or in combination with one or more of the first through fourth implementations, the estimate of the water content associated with the tissue is determined using a tissue absorption model.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A device, comprising:
   one or more memories; and
   one or more processors to:
      obtain, from a multispectral sensor device worn by a subject, measured absorption spectra data associated with the subject,
         wherein the measured absorption spectra data is obtained for a plurality of wavelength channels, and
         wherein the plurality of wavelength channels comprises 16 or more wavelength channels;
      perform fitting of the measured absorption spectra data to a tissue absorption model that is based on:
         mean pathlength of reflected light through tissue,
         wavelength-dependent extinction coefficients for one or more of water, deoxygenated hemoglobin, or oxygenated hemoglobin, and
         one or more concentrations of one or more of water, deoxygenated hemoglobin, or oxygenated hemoglobin that are based on minimizing a sum of squared differences between modeled absorption spectra data and the measured absorption spectra data;
      determine, based on performing fitting of the absorption spectra data to the tissue absorption model, an estimate of a water content associated with the subject;
      determine, based on the estimate of the water content and based on whether the estimate of the water content relates to a skin layer or a muscle layer, an estimate of a hydration level of the subject; and
      cause, based on the estimate of the hydration level of the subject, another device to provide or cease providing fluids to the subject.

2. The device of claim 1, wherein the one or more processors are further to:
   provide the estimate of the hydration level to a user device of a care provider for the subject when the estimate of the hydration level of the subject satisfies a threshold value.

3. The device of claim 1, wherein the device is integrated with the multispectral sensor device.

4. The device of claim 1, wherein the one or more processors are further configured to:
   activate a light source that is directed to the skin layer or the muscle layer based on a first distance between the light source and a light detector of the multispectral sensor device.

5. The device of claim 1, wherein the plurality of wavelength channels are associated with near-infrared light or visible light.

6. The device of claim 1,
   wherein the device is configured to contact a skin surface of the subject, and
   wherein the skin layer includes the skin surface.

7. Wherein the measured absorption spectra data is associated with a wrist of the subject.

8. A non-transitory computer-readable medium storing instructions, the instructions comprising:
   one or more instructions that, when executed by one or more processors, cause the one or more processors to:
      perform fitting of absorption spectra data to a tissue absorption model that is based on:
         mean pathlength of reflected light through tissue,
         wavelength-dependent extinction coefficients for one or more of water, deoxygenated hemoglobin, or oxygenated hemoglobin, and
         one or more concentrations of one or more of water, deoxygenated hemoglobin, or oxygenated hemoglobin that are based on minimizing a sum of squared differences between modeled absorption spectra and measured absorption spectra data;
      determine, based on performing fitting of the absorption spectra data to the tissue absorption model, an estimate of a water content associated with a subject;
      determine, based on the estimate of the water content and based on whether the estimate of the water content relates to a skin layer or a muscle layer, an estimate of a hydration level of the subject; and
      cause, based on the estimate of the hydration level of the subject, another device to provide or cease providing fluids to the subject.

9. The non-transitory computer-readable medium of claim 8, wherein the one or more instructions further cause the one or more processors to:
   transmit a notification to a user device based on whether the estimate of the hydration level of the subject satisfies a threshold value.

10. The non-transitory computer-readable medium of claim 8, wherein the modeled absorption spectra is based on a tissue absorption model that models light scattering and light absorption in tissue.

11. The non-transitory computer-readable medium of claim 8, wherein the one or more instructions, when executed by the one or more processors, further cause the one or more processors to:
    determine the one or more values by minimizing the sum of squared differences between the modeled absorption spectra and the measured absorption spectra data using a nonlinear least squares procedure.

12. The non-transitory computer-readable medium of claim 11, wherein a value, of the one or more values, is constrained by a logistic function that provides a boundary for the value.

13. The non-transitory computer-readable medium of claim 8, wherein the one or more instructions, when executed by the one or more processors, further cause the one or more processors to:
   determine initial values for a tissue absorption model associated with the modeled absorption spectra.

14. A method, comprising:
   obtaining, by a device and from a multispectral sensor device worn by a subject, absorption spectra data that is based on a plurality of light sources that are selectively activated;
   performing, by the device, fitting of the absorption spectra data to a tissue absorption model that is based on:
      mean pathlength of reflected light through tissue,
      wavelength-dependent extinction coefficients for one or more of water, deoxygenated hemoglobin, or oxygenated hemoglobin, and
      one or more concentrations of one or more of water, deoxygenated hemoglobin, or oxygenated hemoglobin that are based on minimizing a sum of squared differences between modeled absorption spectra data and measured absorption spectra data;
   determining, by the device and based on performing fitting of the absorption spectra data to the tissue absorption model, an estimate of a water content associated with the subject;
   determining, by the device, an estimate of a hydration level of the subject based on the estimate of the water content and based on whether the estimate of the water content relates to a skin layer or a muscle layer; and
   causing, by the device and based on the estimate of the hydration level of the subject, another device to provide or cease providing fluids to the subject.

15. The method of claim 14, further comprising at least one of:
   providing the estimate of the hydration level of the subject, or
   transmitting a notification to a user device of a care provider for the subject when the estimate of the hydration level of the subject satisfies a threshold value.

16. The method of claim 14, wherein the estimate of the water content is determined using a tissue absorption model.

17. The device of claim 1, wherein the absorption spectra data is based on a plurality of light sources selectively activated to produce a light intensity needed to reach the skin layer or the muscle layer.

18. The device of claim 1, wherein the multispectral sensor device is a binary multispectral sensor (BMS) device.

19. The method of claim 14, wherein causing the other device to provide or cease providing fluids to the subject comprises:
   causing, based on the estimate of the hydration level of the subject, the other device to cease providing fluids to the subject.

20. The method of claim 14, wherein the plurality of light sources include one or more first light sources that are included in the multispectral sensor device and one or more second light sources that are remotely located from the multispectral sensor device.

* * * * *